United States Patent [19]

Kraus

[11] Patent Number: 6,090,570
[45] Date of Patent: *Jul. 18, 2000

[54] METHOD FOR SPECIFICALLY DETECTING A COAGULATION FACTOR V WHICH HAS AN INCREASED STABILITY TOWARD ACTIVATED PROTEIN C IN THE ACTIVATED STATE

[75] Inventor: Michael Kraus, Marburg, Germany

[73] Assignee: Dade Behring Marburg GmbH, Marburg, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/554,416

[22] Filed: Nov. 8, 1995

[30] Foreign Application Priority Data

Nov. 10, 1994 [DE] Germany .............................. 44 40 097
Feb. 23, 1995 [DE] Germany .......................... 195 06 263

[51] Int. Cl.$^7$ .............................. G01N 33/86; C12Q 1/56
[52] U.S. Cl. ............................ 435/13; 435/7.91; 435/24; 436/63; 436/69
[58] Field of Search ................................ 436/518, 63, 69; 435/13, 7.91, 24; 422/61

[56] References Cited

U.S. PATENT DOCUMENTS 5,051,357   9/1991   Hassouna .................................. 435/13

FOREIGN PATENT DOCUMENTS 44 27 785   of 0000   Germany .
WO 94/17415   8/1994   WIPO .

OTHER PUBLICATIONS

Sun et al., "Blood Coagulation Factor Va Abnormality Associated With Resistance to Activated Protein C in Venous Thrombosis" Blood 83, 3120–3125 (1994). See Materials and Methods.

Charles T. Esmon, "Protein S and Protein C, Biochemistry, Physiology, and Clinical Manifestation of Deficiencies", TCM, 2(6):214–219 (1992).

M.E. Rick et al., "Factor IXa and von Willebrand Factor Modify The Inactivation of Factor VII by Activated Protein C", J. Lab. Clin. Med., 115(4):415–421 (1990).

L. Amer et al., "Impairment of The Protein C Anticoagulant Pathway in a Patient With Systemic Lupus Erythematosus, Anticardiolipin Antibodies and Thrombosis", Thromb. Res., 57(2):247–258 (1990).

R.M. Bertina et al., "Mutation in Blood Coagulation Factor V Associated With Resistance to Activated Protein C", Nature, 369, p. 64–67 (1994).

P. Thiagarajan et al., "The Use of the Dilute Russell Viper Venom Time For Diagnosis of Lupus Anticoagulants", Blood, 68(4):869–874 (1986).

S. Horie et al., "Enhancement of Thrombin–Thrombomodulin–Catalysed Protein C Activation By Phosphatidylethanolamine Containing Unsaturated Fatty Acids: Possible Physiological Significance of Phosphatidylethanolamine in Anticoagulant Activity of Thrombomodulin", Biochem. J., 301, p. 683–691 (1994).

J. Rosing et al., "Inventory of Exogenous Prothrombin Activators", Thrombosis and Haemostatis, 65(5):627–630 (1991).

Bertina et al., "Mutation in Blood Coagulation Factor V Associated with Resistance to Activated Protein C," Nature 369:64–67 (1994).

Karges et al., "Activity of Coagulation and Fibrinolysis Parameters in Animals," Arzneim.–Forsch/Drug Res. 44(1)(6):793–97 (1994).

Kraus et al., "Coagulation Assay with Improved Specificity to Factor V Mutants Insensitive to Activated Protein C," Thrombosis Res. 80(3):255–64 (1995).

*Primary Examiner*—Patricia A. Duffy
*Attorney, Agent, or Firm*—Finnegan, Henderson, Farabow, Garrett & Dunner, L.L.P.

[57] ABSTRACT

Method for specifically detecting a coagulation factor V which has an increased stability toward activated protein C in the activated state.

62 Claims, No Drawings

METHOD FOR SPECIFICALLY DETECTING A COAGULATION FACTOR V WHICH HAS AN INCREASED STABILITY TOWARD ACTIVATED PROTEIN C IN THE ACTIVATED STATE

The invention relates to a method for specifically detecting a coagulation factor V which has an increased stability toward activated protein C in the activated state.

In the first place, the coagulation system in the blood ensures that blood flow is sustained to the tissue which is to be supplied; in the second place, it reacts to injuries by effecting wound closure and thereby ensures that the integrity of the organism is preserved. When coagulation is activated, the active protease thrombin is finally formed by way of a cascade-like system of proteases which activate themselves in a stepwise manner. The formation of thrombin, which is initially very slow, is accelerated by thrombin itself in that the thrombin activates the cofactors factor V and factor VIII by means of proteolytic cleavage. Together with the proteases factor Xa and factor IXa, respectively, these activated cofactors form active enzyme/cofactor complexes on phospholipid surfaces, the activity of which complexes is higher by a factor of approximately 1000 than that of the individual proteases. This positive feedback mechanism gives rise, almost explosively, to the formation of large quantities of thrombin. Thrombin converts fibrinogen into fibrin, normally leading to wound closure and wound healing. In order to prevent a life-threatening spread of the coagulation, which would lead to a closure of the vascular system of the body, that is to thromboses, it is necessary to inhibit the active protease and to prevent the protease being supplied. In the body, active proteases are neutralized by protease inhibitors by means of the formation of covalent complexes. Interruption of the protease supply is initiated by thrombin itself. For this purpose, thrombin binds to the membrane protein thrombomodulin and converts the pro-enzyme protein C into the active protease protein Ca (APC). APC, for its part, forms, together with the cofactor protein S, a complex which proteolytically cleaves, and thereby inactivates, the active cofactors factor VIIIa and factor Va. APC thereby interrupts the powerful stimulating effect produced by these cofactors.

This above-described protein C/protein S system represents an important anticoagulatory mechanism. This is confirmed by the fact that persons with inherited or acquired deficiencies or defects in protein C or protein S are very likely to suffer thromboses, in particular recurring venous thromboses (Esmon, C.T. TCM 2: 214–219, 1992).

Other factors in addition to protein C and protein S are able to exert an influence on the activity of the system. These factors include the von Willebrand factor and factor IXa (Rick, M. E. et al., J. Lab. Clin. Med. 115: 415–421, 1990), which are able to protect factor VIIIa from proteolytic degradation. Acquired impairments can also be due to the formation of lupus anticoagulants. These are antibodies which are directed against phospholipids and which interfere with the binding, which is necessary for their function, of the protease/cofactor complexes to phospholipid surfaces (Amer, L. et al., Thromb. Res. 57: 247–258, 1990).

Very recently, a variant of factor V has been described which, when it is in the activated state (factor Va), can no longer be inactivated, or at least can only be inactivated to a very limit extent, by APC (Bertina, R. M. et al. Nature 369: 64–67, 1994). This defect is also termed "F.V disease" and is due to the replacement of Arg 506 by Gln in the region which is cleaved by APC. Very recently, the importance of this mutation as a cause of increased thrombosis risk has been confirmed in several studies.

Hitherto, two methods have been available for detecting this altered factor V. The first of these is genome analysis by means of the polymerase chain reaction (PCR). As is well known, this method is very elaborate, can only be carried out in specialist laboratories and is relatively expensive. Furthermore, it only detects the previously known mutation. However, it is conceivable that mutations at other sites also stabilize factor Va against cleavage by APC. For this reason, there is an essential requirement for a functional test which supplements the very specialized PCR methodology.

A functional test of this nature, which is based on a known modification (Amer et al., 1990) of the activated partial thromboplastin time (APTT), a screening method customarily employed in coagulation studies, has already been described. In order to determine the APTT in this test, a plasma sample is brought into contact with an equal volume of a reagent which contains a surface activator, for example silica, kaolin or glass, and phospholipids. This mixture is incubated at +37° C. for a few minutes. During this time, those factors of the coagulation system (factor XII, factor XI and factor IX) which are not calcium-dependent are activated. Once calcium ions have been added, the remainder of the coagulation cascade is activated and thrombin is formed. The resulting quantity of thrombin is then determined either by converting the natural substrate fibrinogen into a clot or by liberating a chromophore from a chromogenic substrate. In the modification of this APTT in accordance with Amer, L. et al. (1990), activated protein C is added at the same time as the calcium ions. Since, as described above, APC destroys the cofactors VIIIa and Va, there is a resulting deceleration in thrombin formation, which deceleration is dependent on the functional efficiency of the protein C/protein S system. This modification is termed APC time (APCT) below.

In the form in which it has been used hitherto, the APCT is not suitable for specifically detecting the increased stability of factor v toward APC (see Example 1). In addition to protein C, which is, of course, added exogenously in activated form, all the above-described factors from the sample which exert an effect on the functional efficiency of the protein C/protein S system also enter into the measurement result. Thus, a mutation in factor V, particularly when the patient is heterozygous with regard to this factor, cannot be distinguished from a defect or deficiency in protein S. Antibodies against protein S or protein C can also falsely mimic this effect.

The underlying object of the invention was, therefore, to find a method which can be used to detect factor V which exhibits increased stability toward degradation by APC.

The object is achieved by providing the embodiments described in the patent claims.

It has been found, surprisingly, that when plasmas are diluted with a reagent which is low in factor V and which contains protein S and the coagulation factors X and prothrombin, the influence of protein S can be eliminated whereas the altered stability of factor V toward APC continues to be crucial for the measurement result. In addition to this, heparinized samples, and also samples from patients undergoing marcumar therapy, can be used in this method, which is not possible in the functional tests which have previously been employed.

In the simplest case, the reagent which is used to dilute the sample is human plasma which is deficient in factor V. After activating the factor V in the sample, this factor is destroyed by activated protein C or a protease which behaves in a similar manner, and the residual factor Va activity is determined.

In the simplest case, activation of the factor V in the sample, its destruction, and the detection reaction, are based on triggering coagulation in the sample while adding activated protein C (APC). The proportion of the sample volume represented by the factor V-deficient plasma (F.V-DP) has to be optimized for the particular test method (see examples) and is 50–95%, preferably, however, in the range of 60–80%. This means that, for the total test mixture, the proportion of the plasma sample volume is at most 20%, preferably, however, less than or equal to 10%.

The novel method can thus be based on a modification of the APTT in which the coagulation factors XII, XI and IX are first activated. The formation of thrombin, which activates factor V, is triggered by adding a mixture of APC and calcium chloride. As a result of the simultaneous presence of APC, factor Va is inactivated, resulting in a deceleration in the speed of clot formation. While increasing the proportion of the sample volume represented by factor V-deficient plasma results, on the one hand, in a prolongation of the clotting time, for which the factor V-deficient plasma is responsible, it also results in a decline in the influence exerted by protein S deficiency. Thus, it is demonstrated in Example 2 that once the proportion of the sample volume represented by factor V-deficient plasma has reached approximately 70%, the clotting times for a normal plasma and for a protein S-deficient plasma are the same while, however, the differences in clotting times relative to those of normal plasma increase, if anything, in a homozygous or heterozygous plasma which contains an altered factor V having increased stability toward APC. In this way, it becomes substantially easier to differentiate these two effects than is the case using the prior art.

The thromboplastin time (PT) can also be used instead of the APTT (Example 3). Reagents to be used for measuring PT contain a mixture comprising thromboplastin, a membrane-bound cofactor, phospholipids and calcium chloride. Once this mixture has been added to the sample, factor VII is first cleaved autocatalytically to form factor VIIa. Factor VIIa, together with thromboplastin as cofactor, is then responsible for activating factor X which, in turn, is responsible for forming thrombin, which in turn activates factor V. The clotting time is prolonged in this case as well if activated protein C is added at the same time as the thromboplastin reagent. However, if factor Va is more resistant to proteolytic attack, this prolongation is then less marked. Since this short activation pathway results in the clotting times being very brief, the content of thromboplastin was diluted in Example 3. The resulting prolongation of the clotting time leads to an even more evident prolongation of the clotting time in the presence of APC. This improves the ability to differentiate (signal/background ratio) between normal and altered factor V. Example 3 also demonstrates that the influence exerted by protein S deficiency is neutralized by increasing the extent to which the sample is diluted with factor V-deficient plasma. However, it is necessary to dilute the sample to a greater extent than is the case with the modified APTT.

The novel method can also be employed in a modification of the RVVT (Russell viper venom time). The RVVT is based on using enzymes from the venom of the snake Vipera russellii. This venom contains proteases which activate the human coagulation factors X and V by cleaving them proteolytically. This method, which is known per se, thus circumvents the extrinsic and intrinsic pathways of coagulation and is used both in lupus diagnosis and for detecting deficiencies in factor X, factor V and prothrombin (Thiagarajan, P. et al., 1986). Recently, the method has been employed in association with APC, in the same way as the test based on the APTT, for determining disturbances in the protein C/protein S system. However, it is also the case that other disturbances, for example a deficiency in protein S, give a similar effect in this method to that given by a defect in factor V so that these abnormalities cannot be distinguished from each other in this test. By contrast, Example 4 demonstrates that the abnormalities can be differentiated specifically when the novel method is used, in which case the proportion of the sample volume represented by F.V-DP is preferably 75%.

In addition to achieving specific differentiation, Example 5 demonstrates that any heparin in the sample can be neutralized by adding heparin-neutralizing substances to the F.V-DP. This is another important advantage of the method as compared with the standard method (APCT). Thus, there is particular interest in determining the etiology of the condition in relation to patients with thromboses. However, most of these patients are being treated with anticoagulants, commonly with heparin.

After having been given heparin, many patients who have suffered a thrombosis are placed on marcumar therapy. Marcumar is a vitamin K antagonist and its administration leads to incomplete synthesis of coagulation factors. The investigations described in Example 6 suggest that the novel method can also be used to detect a defect in F.V in patients who are undergoing marcumar therapy.

As an alternative to adding activated protein C, either protein C can be added in the non-activated state or else use can be made of the protein C in the factor V-deficient plasma, which protein C is then activated. This activation can take place, for example, by adding protein C activators obtained from the venoms of the snake of the genus Agkistrodon, as has also been mentioned in German Patent Application P 44 27 785.7 (see Example 7).

When traditional coagulation methods, such as APTT, PT and RVVT, are used, coagulation activity is determined by means of the mechanical, mechanooptical or optical detection of clot formation. The novel method can also be combined with more up to date chromogenic methods, for example by measuring conversion of a chromogenic thrombin substrate.

A reagent system composed of purified coagulation factors can be used instead of F.V-deficient plasma. In analogy with the first variant, the principle of the method is based on factor Va being the rate-limiting factor in prothrombin activation. The simultaneous presence of APC results in the activated factor V being destroyed and, as a result, the clotting time being prolonged. The sample is, therefore, brought into contact with a factor V-dependent prothrombin activator and with a factor V activator, obtained, for example, from the venom of the snake Vipera russellii, and the activation of added prothrombin is measured using methods for the measurement which are known in coagulation diagnosis such as, for example, the conversion of fibrinogen or, in the case of chromogenic methods, the conversion of a chromogenic thrombin substrate.

It is useful to add cofactors which are important for the coagulation enzymes, such as calcium chloride or phospholipids, to the test mixture. It is also useful to add phospholipids at a high concentration, preferably between 0.3 and 0.001%, particularly preferably between 0.001 and 0.01%, in order to eliminate the effect of lupus anticoagulant which is present in the plasma. Moreover, the phospholipids should also contain a proportion of phosphatidylethanolamine in order to ensure that protein Ca activity is expressed (Horie, S. et al., 1994). It is furthermore useful for a reagent system to contain protein S in a concentration range of 0.1–5 U/ml (based on the test mixture), particularly preferably in the range of 1–2 U/ml, in order to avoid interferences with the measurement results which are due to a deficiency of and/or a defect in protein S in the sample. Finally, it is necessary to add activated protein C whose concentration, in the end, regulates the measurement signal. Normally, the concentration of APC in the test mixture will be in the range of 0.01–1 U/ml.

Thus, this reagent system comprises at least the components factor X, protein S, prothrombin, the phospholipids which are required for the coagulation, calcium chloride, activated protein C or, alternatively, non-activated protein C and, separately from it, a protein C activator. The reagent system can either be used combined as a monoreagent or, for increased stability, be used in separated form, such as, for example, as reagent 1, comprising factor X, protein S, prothrombin and phospholipids, and as reagent 2, comprising activated protein C and calcium chloride. The sample is mixed with the reagent system. Coagulation is triggered either as the result of activation of the contact phase, in the same way as in the APTT, or by directly activating factor X and/or factor V using RVV, or by the trace activation of thrombin by means of adding prothrombin-cleaving enzymes such as, for example, active factor X or ecarin from the venom of the snake Echis carinatus. When activation is effected using RVV or ecarin, these enzymes are preferably used together with APC and calcium chloride in reagent 2 as the starting reagent. Detection is then preferably effected by measuring thrombin formation by the conversion of a thrombin-specific, chromogenic substrate.

Moreover, instead of using activated protein C, non-activated protein C can be used which is first activated in the test mixture by means of suitable activators, for example those from the venom of the snake genus Agkistrodon, which venom is commercially obtainable under the tradename PROTAC®. Such a reagent system then comprises, for example, reagent 1 (containing protein S, factor X, protein C, prothrombin and phospholipids) and reagent 2 (containing PROTAC®, RVV, calcium chloride and a thrombin substrate). Reagent 1 can also simply be a factor V-deficient plasma, in which case the phospholipids are then, however, included in reagent 2. In order to amplify the effect of the endogenous protein C, reagent 2 can also be divided and, after preincubating the mixture of sample and reagent 1 with a reagent 2a, comprising PROTAC® and phospholipids, in order to activate the protein C, the coagulation reaction and the reaction for detecting factor v stability can be set in motion by adding-reagent 2b containing RVV and calcium chloride. In this case, the addition of the phospholipids is arbitrary and the further addition of a chromogenic substrate only depends on the evaluation technique which is desired.

Furthermore, in a reagent system composed of purified factors, factor X can be replaced by non-human factor Va-dependent prothrombin activators such as, for example, those obtained from snake venoms (for review, see: Rosing, J. and Tans, G., 1991). This is also suitable, in combination with activated protein C or with protein C which is activated in the test mixture, for specifically detecting a factor V in plasma samples which possesses increased stability toward proteolytic degradation due to activated protein C. Thus, a reagent system might be composed of the following components: reagent 1, comprising protein S, protein C, prothrombin and phospholipids, and reagent 2, comprising PROTAC®, RVV or RVV-V (the protease from RVV which activates only factor V), factor V-dependent prothrombin activator, calcium chloride and a thrombin substrate, or, alternatively, the thrombin substrate as reagent 3.

Reagent systems which are based on an APTT are dependent on the concentration of factor VIII in the sample, as mentioned in Example 8. It has been found, surprisingly, that a factor V-deficient plasma which contains factor VIII at physiological concentrations (0.7–1.4 units/ml) is less dependent on the concentration of factor VIII in the sample than is a deficient plasma which does not contain any factor VIII. This makes it easier to differentiate between normal plasmas having a high content of factor VIII and factor V disease plasmas having a normal content of factor VIII. For this reason, factor V-deficient plasma and/or reagents which either contain, or which are supplemented with, factor VIII at concentrations of between 0 and 4 U/ml, particularly preferably in the concentration range of between 0.7 and 1.3 U/ml, are preferably used in reagent systems which are based on an APTT.

The following examples are intended to illustrate the invention without, however, limiting the claims in any way.

Abbreviations employed:

| | |
|---|---|
| APCT | activated protein C time |
| APCV | activated protein C time when mixing the sample with factor V-deficient plasma |
| APTT | activated, partial thromboplastin time |
| Arg | arginine |
| F.V-DP | human factor V-deficient plasma |
| F.V disease | amino acid exchange Arg → Gln at position 506 in factor V |
| Gln | glutamine |
| PC-DP | human protein C-deficient plasma |
| PS-DP | human protein S-deficient plasma |
| RVVT | Russell viper venom time |
| SHP | standard human plasma (a pool of normal human plasma) |
| Tris | tris(hydroxymethyl)aminomethane |

EXAMPLE 1

The Limitation of the State of the Art with Regard to the Functional Detection of F.V Disease or a Similar Defect The clotting time was determined using an automated coagulometer (Behring Fibrintimer A, Behringwerke; from Behringwerke AG, Marburg). All the reagents were obtained from Behringwerke AG. SHP was used as a plasma pool from healthy blood donors.

The APTT is determined in accordance with the following protocol: 1 vial of PATHROMTIN®, a phospholipid mixture from human placenta, for 5 ml was dissolved in 5 ml of a suspension of kaolin as the surface activator. The calcium chloride solution (25 mM) was warmed to +37° C. before use.

The following were pipetted consecutively into a measuring tube

100 μl of PATHROMTIN®

100 μl of plasma sample.

The mixture was subsequently incubated at +37° C. for 2 minutes and the clotting time was started by adding 100 μl of calcium chloride solution. The clotting time was determined at 405 nm.

The APCT was determined using the APC sensitivity reagents from Behringwerke. The activator reagent was prepared in the same way as for the APTT. The starting reagent composed of calcium chloride and activated protein C was dissolved in 5 ml of distilled water and warmed to +37° C. before use.

The following were pipetted consecutively into a measuring tube

100 µl of PATHROMTIN®
100 µl of plasma sample.

The mixture was subsequently incubated at +37° C. for 2 minutes and the clotting time was started by adding 100 µl of starting reagent. The clotting time was determined at 405 nm.

The APTT and APCT were determined in the following human citrate plasmas: in a pool from healthy blood donors (SHP), in plasmas deficient in protein C (PC-DP) or protein S (PS-DP), and in a plasma having a homozygous F.V disease defect. In order to simulate a heterozygous defect, in which approximately 50% of the factor V in the plasma is present in the intact form and approximately 50% is present in the F.V disease form, the homozygous F.V disease plasma was mixed 1:1 with SHP.

The clotting times obtained, and the differences in the APCTs as compared with the clotting time obtained with SHP, are presented in Table 1. The values for the APTTs were all within the normal range (≦40 sec), which is a prerequisite for carrying out the APCT. In the APCT, those clotting times are pathological which are shorter than the clotting time obtained with normal plasma. This does not apply in the case of protein C deficiency. Since, in the APCT, activated protein C is added exogenously, the protein C in the sample cannot have an effect on the test. On the other hand, protein S deficiency results in a shortening of the clotting time which, in this case, is even more marked than it is with a heterozygous F.V disease defect. The shortening of the APCT is most pronounced in the case of a homozygous F.V disease defect. There is only a slight difference in the effect of protein S deficiency and a homozygous F.V disease defect. In practice, this difference becomes even more blurred since there is a continuous denaturation of factors V and VIII, the extent of which depends on the time elapsing between removal of the blood sample and the determination. This factor denaturation leads to a prolongation of the clotting time which counteracts the shortening of the clotting time which is observed.

Consequently, the previously available method, i.e. APCT, is not suitable for specifically detecting a F.V disease defect or a similar defect in factor V which leads to increased stability toward activated protein C.

Table 1: APTTs and APCTs of different plasmas with deficiencies or defects which affect the functional efficiency of the protein C/protein S system. The table gives the (absolute) clotting times, and the differences in the APCTs as compared with the clotting time obtained with SHP, in seconds. SHP=normal plasma; PC-DP=protein C-deficient plasma, PS-DP=protein S-deficient plasma, F.V-D1/1= plasma with homozygous F.V disease defect, F.V-D1/2= plasma with heterozygous F.V disease defect.

| Plasma | Absolute | | Difference |
| --- | --- | --- | --- |
| | APTT | APCT | APCT |
| SHP | 34.0 | 120.6 | — |
| PC-DP | 38.9 | 216.1 | 95.5 |
| PS-DP | 37.6 | 78.9 | −41.7 |
| F.V-D1/2 | 34.8 | 83.7 | −36.9 |
| F.V-D1/1 | 32.5 | 61.8 | −58.8 |

EXAMPLE 2

Optimizing the Novel Method Based on a Modified APTT

The clotting time was determined using an automated coagulometer (Behring Fibrintimer A, Behringwerke; from Behringwerke AG, Marburg). All the reagents were obtained from Behringwerke AG. SHP was used as a plasma pool from healthy blood donors.

For determining clotting time, 1 vial of PATHROMTIN® for 5 ml was dissolved in 5 ml of kaolin suspension. The starting reagent comprising the APC sensitivity reagents (containing calcium chloride and activated protein C) was dissolved in 5 ml of distilled water and warmed to +37° C. before use. Factor V-deficient plasma was dissolved in 1 ml of distilled water.

The following were pipetted consecutively into a measuring tube x µl of plasma sample
y µl of F.V-DP
100 µl of PATHROMTIN®

The mixture was subsequently incubated at +37° C. for 3 minutes, and the clotting time was started by adding 100 µl of starting reagent. The clotting time was determined at 405 nm.

The volumes x and y were chosen such that the total volume (x+y) amounted to exactly 100 µl. The clotting times were determined in the following human citrate plasmas: in a pool from healthy blood donors (SHP), in plasmas with a deficiency of protein C (PC-DP) or protein S (PS-DP), and in a plasma with a homozygous F.V disease defect. In order to simulate a heterozygous defect, in which approximately 50% of the factor V in the plasma is present in the intact form and approximately 50% is present in the F.V disease form, the homozygous F.V disease plasma was mixed 1:1 with SHP.

The clotting times which were obtained, and the differences in the clotting times relative to the clotting time obtained with SHP, are listed in Table 2. As the proportion of the sample volume represented by F.V-DP increases, the clotting times become longer due to the increasing deficiency of factor V. However, while the difference between SHP and PC-DP remains virtually unaltered, the gap between SHP and PS-DP reduces continuously and, once the proportion of F.V-DP in the test mixture has reached approximately 70%, a difference can no longer be detected. The deficiency of protein S in the sample is, therefore, adequately neutralized by the protein S in the F.V-DP. However, the plasmas with homozygous or (simulated) heterozygous F.V disease defects behave in precisely the opposite manner. In these cases, the differences in clotting times as compared with the clotting times obtained with SHP increase.

Thus, the novel method not only makes it possible to eliminate the effect of PS deficiency, but also actually amplifies the effect caused by F.V disease. This also means that disturbances due to storing the plasma samples for relatively long periods of time will not so readily lead to a blurring of the difference between a PS deficiency and a F.V defect as has been the case using previous methods (Example 1). Furthermore, it is to be expected that anti-PS autoantibodies will be neutralized in this method since, of course, the PS effect is eliminated. Furthermore, autoantibodies against PC or PC/PS phospholipid complexes should scarcely be detectable when the sample is highly diluted with the F.V-DP, simply as a result of this dilution.

Table 2: The effect of the proportion of the sample volume represented by F.V-DP on the clotting times of different plasmas with deficiencies or defects which affect the functional efficiency of the protein C/protein S system in the novel method based on a modified APTT. The table gives the clotting times (A) which were obtained, and the differences (B) in the clotting times relative to the clotting times obtained with SHP, in seconds, SHP=normal plasma; PC-DP=protein C-deficient plasma, PS-DP=protein S-deficient plasma, F.V-D1/1=plasma with homozygous F.V disease defect, F.V-D1/2=plasma with heterozygous F.V disease defect.

|  | Proportion of F.V-deficient plasma | | | |
|---|---|---|---|---|
| Plasma | 50% | 60% | 70% | 75% |
| (A) | | | | |
| SHP | 130.9 | 149.7 | 171.1 | 184.3 |
| PC-DP | 181.3 | 194.8 | 183.7 | 231.5 |
| PS-DP | 109.8 | 140.0 | 175.5 | 198.3 |
| F.V-D1/1 | 69.1 | 78.1 | 89.0 | 98.2 |
| F.V-D1/2 | 90.3 | 100.9 | 114.8 | 124.9 |
| (B) | | | | |
| PC-DP | 50.4 | 45.1 | 12.6 | 47.2 |
| PS-DP | −21.1 | −9.7 | 4.4 | 14.0 |
| F.V-D1/1 | −61.8 | −71.6 | −82.1 | −86.1 |
| F.V-D1/2 | −40.6 | −48.8 | −56.3 | −59.4 |

EXAMPLE 3
Optimizing the Novel Method Based on a Modified Thromboplastin Time

The clotting time was determined using an automated coagulometer (Behring Fibrintimer A, Behringwerke; from Behringwerke AG, Marburg). All the reagents were obtained from Behringwerke AG. SHP was used as a plasma pool from healthy blood donors.

For determining the clotting time, THROMBOPLASTIN®, a PT reagent from human placenta, was, in accordance with the manufacturer's instructions, dissolved in distilled water with this solution then being diluted 1:2000 with a buffer comprising 50 mM tris/HCl, 0.01% Phospholipon-25 (a phospholipid mixture from soya beans), 10 mM calcium chloride, 0.4 U/ml APC, pH 7.4. The reagent was warmed to +37° C. before use. Factor V-deficient plasma was dissolved in 1 ml of distilled water.

The following were pipetted consecutively into a measuring tube x µl of plasma sample y µl of F.V-DP 100 µl of THROMBOPLASTIN® 1:2000

The mixture was subsequently incubated at +37° C. for 3 minutes, and the clotting time was started by adding 100 µl of starting reagent. The clotting time was determined at 405 nm.

The volumes x and y were chosen such that the total volume (x+y) amounted to exactly 100 µl. Under these circumstances, the variant containing 0 µl of F.V-DP corresponds to a variant of the APCT based on the thromboplastin time. The clotting times were determined in the same samples as in Example 2.

Table 3 lists the clotting times which were obtained and also the differences in the clotting times relative to the clotting times obtained with SHP.

As the proportion of the sample volume represented by F.V-DP increases, the clotting times become longer due to the increasing deficiency in factor V. Nevertheless, it was not possible to neutralize the effect of protein S completely even when the proportion of the sample volume represented by F.V-DP amounted to 75%, so that even higher concentrations have to be used. Moreover, there is still further scope for optimizing the reactivity by appropriate choice of buffering substances, ionic strengths and phospholipid concentration. Despite this, it can be seen that the differences between the clotting times for PS-DP and both homozygous and heterozygous F.V disease become larger and that it therefore becomes easier to differentiate between the two disturbances of the protein C/PS system when the novel method is used, even when the latter is based on PT.

Table 3: Effect of the proportion of the sample volume represented by F.V-DP on the clotting times of different plasmas with deficiencies or defects which affect the functional efficiency of the protein C/protein S system in the novel method based on a modified PT. The table gives the clotting times (A) which were obtained, and the differences (B) in the clotting times relative to the clotting times obtained with SHP, in seconds. SHP=normal plasma; PC-DP=protein C-deficient plasma, PS-DP=protein S-deficient plasma, F.V-D1/1=plasma with homozygous F.V disease defect, F.V-D1/2=plasma with heterozygous F.V disease defect.

|  | Proportion of F.V deficient plasma | | | | |
|---|---|---|---|---|---|
| Plasma | 50% | 60% | 70% | 75% | 80% |
| (A) | | | | | |
| SHP | 128.1 | 138.9 | 148.3 | 160.0 | 171.4 |
| PC-DP | 151.7 | 189.7 | 179.2 | 202.5 | 224.1 |
| PS-DP | 75.7 | 83.3 | 104.3 | 121.4 | 144.3 |
| F.V-D1/1 | 67.7 | 70.0 | 83.3 | 89.2 | 104.4 |
| F.V-D1/2 | 74.8 | 78.6 | 87.7 | 98.8 | 120.2 |
| (B) | | | | | |
| PC-DP | 23.6 | 50.8 | 30.9 | 42.5 | 52.7 |
| PS-DP | −52.4 | −55.6 | −44.0 | −38.6 | −27.1 |
| F.V-D1/1 | −60.4 | −68.9 | −65.0 | −70.8 | −67.0 |
| F.V-D1/2 | −53.3 | −60.3 | −60.6 | −61.2 | −51.2 |

EXAMPLE 4
Optimizing the Novel Method Based on a Modified RVV Time

The clotting time was determined using an automated coagulometer (Behring Fibrintimer A, Behringwerke; from Behringwerke AG, Marburg). The reagent LA-CONFIRM® from Gradipore, Australia, was used as the RVV reagent. All the other reagents were obtained from Behringwerke AG.

In order to determine the clotting time, 1 vial of LA-CONFIRM® for 2 ml was dissolved in 2 ml of starting reagent from the APC sensitivity reagents (containing calcium chloride and activated protein C), and this solution was warmed to +37° C. before use (=RVV/APC reagent). Factor V-deficient plasma was dissolved in 1 ml of distilled water.

The following were pipetted consecutively into a measuring tube x µl of plasma sample y µl of F.V-DP, and the clotting time was started by adding 100 µl of RVV/APC reagent. The clotting time was determined at 405 nm.

The volumes x and y were chosen such that the total volume (x+y) amounted to exactly 100 µl. Under these circumstances, the variant containing 0 µl of F.V-DP corresponds to a variant of the APCT based on the RVV assay. The clotting times were determined in the same samples as in Example 2.

Table 4 lists the clotting times which were obtained and also the differences in the clotting times relative to the clotting times obtained with SHP. As in the other test variants (Examples 2 and 3), the clotting times become more prolonged as the proportion of F.V-DP in the sample volume increases. Protein C-deficient plasma is always prolonged as compared with SHP. While the difference between SHP and protein S-deficient plasma becomes smaller with increasing proportion of F.V-DP, the effect of F.V disease becomes greater. In a similar manner to the test variant based on PT (Example 3), the protein S deficiency is not completely neutralized using the proportions of F.V-DP listed here, so that a proportion of F.V-DP must be chosen which is even greater than 70%.

However, the differences between a plasma with F.V disease, whether homozygous or heterozygous, and a plasma with a protein S deficiency or defect become more pronounced so that, on the basis of RVVT as well, the novel method leads to an increased ability to differentiate a factor V which is more stable toward activated protein C from other disturbances of the protein C/protein S system.

Table 4: The effect of the proportion of the sample volume represented by F.V-DP on the clotting times of different plasmas with deficiencies or defects which affect the functional efficiency of the protein C/protein S system in the novel method based on a modified RVVT. The table gives the clotting times (A) which were obtained, and also the differences (B) in clotting times relative to the clotting times obtained with SHP, in seconds. SHP=normal plasma; PC-DP=protein C-deficient plasma, PS-DP=protein S-deficient plasma, F.V-D1/1=plasma with homozygous F.V disease defect, F.V-D1/2=plasma with heterozygous F.V disease defect.

|  | Proportion of F.V-deficient plasma | | | |
| --- | --- | --- | --- | --- |
| Plasma | 50% | 60% | 70% | 75% |
| (A) | | | | |
| SHP | 93.8 | 101.1 | 109.2 | 121.1 |
| PC-DP | 122.4 | 127.4 | 139.2 | 149.4 |
| PS-DP | 73.2 | 82.8 | 94.0 | 107.7 |
| F.V-D1/1 | 48.7 | 53.2 | 60.0 | 67.2 |
| F.V-D1/2 | 58.1 | 63.3 | 71.1 | 79.2 |
| (B) | | | | |
| PC-DP | 28.6 | 26.3 | 30.0 | 28.3 |
| PS-DP | −20.6 | −18.3 | −15.2 | −13.4 |
| F.V-D1/1 | −45.1 | −47.9 | −49.2 | −53.9 |
| F.V-D1/2 | −35.7 | −37.8 | −38.1 | −41.9 |

EXAMPLE 5
Neutralizing Heparin by Making Additions to the Factor V-deficient Plasma Heparin was obtained from Hoffman-La Roche, Grenzach-Wyhlen, (LIQUEMIN® 25000), while hexadimethrine-bromide (POLYBRENE®) was obtained from Ega-Chemie, Steinheim. The remaining reagents and apparatus were obtained from Behringwerke AG.

Heparin was added to standard human plasma and to a plasma with a factor V disease defect, and the clotting times were determined in the novel method, as described under Example 2, using a proportion of F.V-DP in the sample volume of 75%. In addition, hexadimethrine-bromide (POLYBRENE®) was added, at the rate of 10 μg/ml, to the factor V-deficient plasma in order to neutralize the heparin in the sample.

Table 4 lists the clotting times which were obtained in the different test variants in the presence of from 0 to 2 U/ml heparin. When the F.V-DP does not contain any heparin-neutralizing addition, the clotting times deviate markedly from that of the sample without heparin once heparin is present at a concentration greater than 0.2 U/ml. The addition of 10 μg/ml hexadimethrine-bromide (POLYBRENE®) to the F.V-DP renders it possible to measure the factor V defect even in the presence of up to 2 U/ml heparin. This demonstrates that, in contrast to the prior art, it is possible to determine the F.V disease defect even in heparinized samples.

Table 5: Neutralizing heparin in a normal plasma and in a plasma with a factor V disease defect by adding hexadimethrine-bromide (POLYBRENE®) in the novel method. The table gives the clotting times in seconds. SHP=normal plasma; F.V-D=plasma with homozygous F.V disease defect.

| Heparin | SHP | | F.V-D | |
| --- | --- | --- | --- | --- |
| (IU/ml) | −PB | +PB | −PB | +PB |
| 0 | 185.0 | 195.7 | 96.8 | 100.9 |
| 0.2 | 206.4 | 190.5 | 104.1 | 101.8 |
| 0.4 | >300 | 195.3 | 143.2 | 100.0 |
| 0.6 | >300 | 193.8 | >300 | 100.3 |
| 0.8 | >300 | 198.9 | >300 | 99.6 |
| 1.0 | >300 | 198.9 | >300 | 100.3 |
| 1.2 | >300 | 196.6 | >300 | 101.2 |
| 1.4 | >300 | 195.5 | >300 | 100.4 |
| 1.6 | >300 | 200.5 | >300 | 99.7 |
| 1.8 | >300 | 201.0 | >300 | 100.2 |
| 2.0 | >300 | 201.0 | >300 | 101.6 |

EXAMPLE 6
Determining the F.V Defect in the Plasma of Patients Undergoing Marcumar Therapy The APCTs of 9 plasmas from patients who were not being given either marcumar or heparin and of 6 plasmas from patients who were undergoing marcumar therapy following thromboses were measured in accordance with Example 1, as were the APCVs of these plasma samples in accordance with Example 2 and using a proportion of F.V-DP in the sample volume of 75%.

The clotting times which were obtained are listed in Table 6. The results were converted into % relative to the clotting times which were obtained with SHP (=100%). In both tests, those samples are positive which lie below the 100% boundary. The non-marcumarized plasmas were positive in both tests, i.e. were found to lie below the 100% boundary; by contrast, while all the marcumarized plasmas were negative in the APCT, 5 out of the 6 plasmas clearly lay below this boundary in the novel method (APCV). As a result of the mixing with the F.V-DP, all the defective, vitamin K-dependent enzymes in the marcumarized plasmas are replaced. The clotting times are also shortened when the plasmas are mixed with normal plasma (Table 6). However, this does not suffice to enable positive samples to be identified in the APCT using samples in which replacement has taken place in this way. Therefore, the novel method is superior to the prior art.

Table 6: Reaction behavior of plasmas with F.V disease defect and of marcumarized plasmas from patients following thromboses in the APCT and in the APCV. The table gives the clotting times relative to the clotting times obtained with SHP (=100) in %. F.V-D=plasmas with homozygous F.V disease defect, Marc=marcumarized plasmas, Marc/SHP=marcumarized plasmas mixed 1/1 with normal, non-marcumarized plasma.

|   | APCT |   |   | APCV |   |
| --- | --- | --- | --- | --- | --- |
| F.V-D | Marc | Marc/SHP | F.V-D | Marc | Marc/SHP |
| 60.3 | 196.6 | 99.9 | 60.6 | 74.6 | 85.1 |
| 46.6 | 198.5 | 100.4 | 46.6 | 74.4 | 84.4 |
| 48.9 | 219.7 | 103.8 | 51.5 | 81.2 | 90.3 |
| 42.4 | 143.9 | 96.7 | 44.0 | 82.3 | 88.0 |
| 44.6 | 245.5 | 74.7 | 46.5 | 58.6 | 104.9 |
| 56.1 | 180.0 | 110.6 | 52.8 | 105.6 | 99.2 |
| 54.3 |   |   | 54.4 |   |   |
| 49.2 |   |   | 51.2 |   |   |
| 62.4 |   |   | 55.9 |   |   |

EXAMPLE 7
Determining the F.V Defect by Activating the Protein C in the Added Factor V-deficient Plasma The clotting time was measured using an automated coagulometer (Behring Fibrintimer A, Behringwerke; from Behringwerke AG, Marburg). All the reagents were obtained from Behringwerke AG.

In order to determine the clotting time, 1 vial of protein activator reagent for protein C reagents from Behringwerke was dissolved in the content of 1 vial of PATHROMTIN® SL (an APTT reagent based on silica; 5.5 ml). This reagent, and the calcium chloride solution (25 mM), were warmed to +37° C. before use. Factor V-deficient plasma was dissolved in 1 ml of distilled water.

The following were pipetted consecutively into a measuring tube x µl of plasma sample y µl of F.V-DP 100 µl of protein C activator/PATHROMTIN® SL mixture.

The whole mixture was subsequently incubated at +37° C. for 3 minutes, and the clotting time was started by adding 100 µl of starting reagent. The clotting time was determined at 405 nm.

The volumes x and y were chosen such that the total volume (x+y) amounted to exactly 100 µl. Under these circumstances, the variant containing 0 pl of F.V-DP corresponds to a new screening test for disturbances of the protein C/protein S system, as described in German Patent Application P 44 27 785.7. The clotting times were determined in the same samples as in Example 2.

Table 7 lists the clotting times which were obtained and also the differences in the clotting times relative to the clotting times obtained with SHP. As in the other test variants (Examples 2 to 4), the clotting times become more prolonged as the proportion of F.V-DP in the sample volume increases. While the differences between SHP and protein S-deficient plasma become smaller as the proportion of F.V-DP increases, the effect of the F.V disease becomes greater. The effect of the deficit in protein S is neutralized when the proportion of F.V-DP in the sample volume is 70%. The results thus have equal standing with the applications of the novel method which were demonstrated in Examples 2 to 4, although no activated protein C was added in this case but, instead, non-activated protein C was added which was then activated in the test mixture.

Table 7: Clotting times of different plasmas with deficiencies or defects which affect the functional efficiency of the protein C/protein S system in the novel method based on a modified APTT, with protein C being first activated in the test mixture. The table gives the clotting times (A) which were obtained, and the differences (B) in the clotting times relative to the clotting times obtained with SHP, in seconds. SHP=normal plasma; PC-DP=protein C-deficient plasma, PS-DP=protein S-deficient plasma, F.V-D1/1=plasma with homozygous F.V disease defect, F.V-D1/2=plasma with heterozygous F.V disease defect.

|   | Proportion of F.V-deficient plasma | | | |
| --- | --- | --- | --- | --- |
| Plasma | 50% | 60% | 70% | 75% |
| (A) |   |   |   |   |
| SHP | 154.9 | 170.0 | 195.0 | 207.2 |
| PC-DP | 176.4 | 206.6 | 263.7 | 274.4 |
| PS-DP | 122.5 | 156.0 | 196.3 | 241.2 |
| F.V-D1/1 | 69.4 | 78.9 | 93.6 | 103.4 |
| F.V-D1/2 | 94.7 | 104.4 | 125.7 | 131.3 |
| (B) |   |   |   |   |
| PC-DP | 21.5 | 36.6 | 68.7 | 67.2 |
| PS-DP | −32.4 | −14.0 | 1.3 | 34.0 |
| F.V-D1/1 | −85.5 | −91.1 | −101.4 | −103.8 |
| F.V-D1/2 | −60.2 | −65.6 | −69.3 | −75.9 |

EXAMPLE 8
Dampening the effect of the factor VIII in the sample in an APTT-dependent method by adding factor VIII to a factor V-deficient plasma.

The clotting time was determined using an automated coagulometer (Behring Fibrintimer A, Behringwerke; from Behringwerke AG, Marburg). All the reagents were obtained from Behringwerke AG. BERIATE®, a concentrate of human factor VIII from Behringwerke, was used as the source of factor VIII.

The test was carried out using the method described in Example 2, mixing the sample and the factor V-deficient plasma in the ratio of 25:75. A heat-inactivated human plasma was used as the factor V-deficient plasma. Both factor V and factor VIII are destroyed in this inactivation. For comparison, this plasma, after having been dissolved, was supplemented with factor VIII, using BERIATE®, to a concentration of 1 unit per ml. In addition, SHP was supplemented with factor VIII from BERIATE® so that the content of factor VIII in the SHP amounted to between 1 and 4 units/ml. A human plasma with heterozygous factor V disease defect was measured in the novel method for comparison.

Table 8 lists the clotting times, and also the differences in the clotting times relative to those obtained with SHP containing 1 unit/ml factor VIII, which were obtained using the factor V-deficient plasma with and without factor VIII supplementation. When the factor VIII-free deficient plasma is used, the clotting times in the normal plasma become shorter as the content of factor VIII in the plasma increases and approach those which are obtained with a plasma with factor V disease defect but with a normal content of factor VIII. On the other hand, if the factor V-deficient plasma already contains 1 U/ml factor VIII, the shortening of the clotting time due to the content of factor VIII in the sample becomes negligible.

This demonstrates that it is possible, in a test design based on an APTT, to prevent samples being falsely identified as positive due to their elevated levels of factor VIII by adding factor VIII or by using factor VIII-containing reagents.

Table 8: The effect of the content of factor VIII on the clotting times of normal plasma when using factor V-deficient plasma without factor VIII (0 F.VIII) or when using a factor V-deficient plasma containing 1 unit of factor VIII per ml. In addition to giving the clotting times for normal plasma (SHP) containing different concentrations of factor VIII (1 to 4 U/ml), the table also gives the clotting times for plasma with heterozygous F.V disease defect (F.V disease), and the differences relative to the normal plasma containing 1 U of factor VIII/ml. Values in seconds.

|  | Absolute values | | Differences | |
| --- | --- | --- | --- | --- |
| SHP | 0 F.VIII | 1 U/ml F.VIII | 0 F.VIII | 1 U/ml F.VIII |
| 1 | 181.8 | 76.9 | 0.0 | 0.0 |
| 1.5 | 150.9 | 75.3 | −30.9 | −1.6 |
| 2 | 134.2 | 73.7 | −47.6 | −3.2 |
| 2.5 | 123.3 | 73.1 | −58.5 | −3.8 |
| 3 | 116.1 | 72.1 | −65.7 | −4.8 |
| 4 | 109.7 | 69.6 | −72.1 | −7.3 |
| F.V disease | 85.7 | 48.4 | −96.1 | −28.5 |

What is claimed is:

1. A method for the determination of the stability of a coagulation factor v (F V) in its activated form (F Va) toward proteolytic degradation in a sample of a biological fluid, which method includes the following steps:
 a) mixing the sample with a reagent A, which has a lower content of functional F V than normal, human plasma;
 b) adding a reagent B which activates F V in the sample;
 c) adding a reagent C for proteolytically degrading the F Va in the sample;
 d) adding reagents necessary for determining F Va activity; and
 e) determining the activation of prothrombin to form thrombin by either detection of clot formation or by measuring conversion of a chromogenic thrombin substrate;
 wherein
  i) the volume of the sample of a biological fluid is 20% or less of the total volume of sample and all reagents added to the sample (test mixture); and
  ii) the steps a) through d) are performed without being interrupted by periods for incubating the resulting mixtures.

2. The method as claimed in claim 1, wherein the reagent A is F V-deficient plasma of human or animal origin.

3. The method as claimed in claim 2, wherein in reagent A is a plasma that is FV-deficient because
 a) the amount of FV is diminished compared to a normal human plasma or
 b) the FV in the plasma is such that it cannot be activated in the activation procedure which is employed.

4. The method as claimed in claim 3, wherein the diminished amount of F V in the plasma is due either to a genetic deficiency or defect.

5. The method as claimed in claim 3, wherein the diminished amount of F V in the plasma was produced by adsorption on suitable high-affinity binding partners.

6. The method as claimed in claim 5, wherein the adsorption on high-affinity binding partners takes place on support materials coated with antibody against factor V.

7. The method as claimed in claim 5, wherein the diminished content of factor V is produced by immunoadsorption using monoclonal antibodies against factor V.

8. The method as claimed in claim 3, wherein the F V of the plasma employed was inactivated by prior treatment.

9. The method as claimed in claim 8, wherein the prior treatment comprises heat treatment used to denature the factor V.

10. The method as claimed in claim 3, wherein the amount of F V of the plasma employed was diminished by prior treatment with proteolytic enzymes which specifically inactivate F V or F Va.

11. The method as claimed in claim 3, wherein the F V which is present in the plasma cannot be activated by the reagent B.

12. The method as claimed in claim 3, wherein the concentration of functional content of F V present in the plasma is between 0 and 50% of normal human plasma.

13. The method as claimed in claim 12, wherein the content is less than 10% of the content of a normal human plasma.

14. The method as claimed in claim 3, wherein the FV-deficient plasma contains Factor VIII at concentrations of between 0 and 4 U/ml.

15. The method as claimed in claim 14, wherein the concentration of factor VIII is between 0.7 and 1.3 U/ml.

16. The method as claimed in claim 1, wherein the proportion of the F V-deficient plasma in the any of steps a to d is between 50–95%.

17. The method as claimed in claim 16, wherein the proportion of the F V-deficient plasma is between 60–80% of normal human plasma.

18. The method as claimed in claim 1, wherein reagent A further comprises additives for neutralizing heparin.

19. The method as claimed in claim 18, wherein said additive is hexadimethrine-bromide and is used at concentrations of between 2 and 50 mg/l.

20. The method as claimed in claim 18, wherein said additive is hexadimethrine-bromide and is used at concentrations of between 10 and 20 mg/l.

21. The method as claimed in claim 1, wherein the reagent A with which the sample is mixed is water, physiological sodium chloride solution, a suitable buffer solution and/or an individual enzyme or cofactor or several of these enzymes and co-factors, which are not identical to F V or F Va.

22. The method as claimed in claim 21, wherein any of the reagents A to C contain an amount of factor VIII that is in the range of from 0.01 to 2 units/ml.

23. The method as claimed in claim 22, wherein the concentration of the reagent containing factor VIII is in the range of from 0.7 to 1.3 units/ml.

24. The method as claimed in claim 21, wherein reagent A contains a concentration of protein S in the range of 0.2–5 U/ml based on the concentration after mixing with the sample.

25. The method as claimed in claim 24, wherein the concentration of protein S is in the range of 0.5–2 U/ml.

26. The method as claimed in claim 21, wherein reagent A contains a concentration of factor X in the range of 0.2–5 U/ml based on the concentration after mixing with the.

27. The method as claimed in claim 26, wherein the concentration of factor X is in the range of 0.5–2 U/ml.

28. The method as claimed in claim 21, wherein reagent A contains a concentration of prothrombin in the range of 0.5–10 U/ml based on the concentration after mixing with the sample.

29. The method as claimed in claim 28, wherein the concentration of prothrombin is in the range of 1.0–2 U/ml.

30. The method as claimed in claim 1, wherein any of the reagents A to C contain an amount of a substance selected from the group consisting of phospholipids and mixtures of phosphatidylcholine, phosphatidylserine and phosphatidylethanolamine, such that the concentration in any of reagents A to C is in the range of 0.3–0.001%.

31. The method as claimed in claim 30, wherein the phospholipids are mixtures of phosphatidylcholine, phosphatidylserine and phosphatidylethanolamine.

32. The method as claimed in claim 30, wherein the concentration of phospholipids are in the range of 0.01–0.1%.

33. The method as claimed in claim 1, wherein the reagent C comprises proteolytic enzymes of human or animal origin.

34. The method as claimed in claim 19, wherein thrombin is used as the enzyme of human origin.

35. The method as claimed in claim 33, wherein the enzymes used are of animal origin.

36. The method as claimed in claim 33, wherein the proteolytic enzyme of human origin is human protein C.

37. The method as claimed in either claim 2 or 36, wherein human protein C is added in non-activated form.

38. The method as claimed in claim 36, wherein the human protein C is added to step C in activated form at a concentration of 0.02–1 U/ml based on the test mixture.

39. The method as claimed in claim 38, wherein the human protein C is added at a concentration of 0.05–0.15 U/ml.

40. The method as claimed in either claim 2 or 36, wherein human protein C is present in the F V-deficient plasma.

41. The method as claimed in claim 1, wherein the F V of the sample is indirectly activated by triggering the coagulation cascade by means of activating a contact phase using surface activators, phospholipids and calcium ions in accordance with the method of the activated, partial thromboplastin time (APTT).

42. The method as claimed in claim 1, wherein the F V of the sample is activated by triggering the coagulation cascade by means of adding thromboplastin, phospholipids and calcium ions in accordance with the method of the thromboplastin time (PT).

43. The method as claimed in claim 1, wherein the F V of the sample is indirectly activated by means of activating prothrombin by adding thrombin-activating substances to step b.

44. The method as claimed in claim 43, wherein the thrombin-activating substances are obtained from the venom of the snake *Echis carinatus*.

45. The method as claimed in claim 1, wherein at least one of the reagents contains a protein C-activating enzyme which comes into contact with the sample and activates human non-activated protein C present in the sample.

46. The method as claimed in claim 45, wherein the protein C-activating enzyme is from the venom of the snake genus Agistrodon.

47. The method as claimed in claim 1, wherein activation of prothrombin to thrombin is determined by clot formation by measuring the conversion of fibrinogen using mechanical, optical or optomechanical methods.

48. The method as claimed in claim 47, wherein activation of prothrombin to thrombin is determined by measuring the conversion of a thrombin-specific, chromogenic substrate by means of optical detection.

49. The method as claimed in claim 47, wherein the fibrinogen is contained in the sample.

50. The method as claimed in claim 47, wherein the fibrinogen is contained in the reagents of step d) with which the sample is mixed.

51. The method as claimed in claim 1, wherein prothrombin is activated by a prothrombin activator present in any one of the reagents, wherein the prothrombin activator can be stimulated by FVa.

52. The method as claimed in claim 51, wherein human factor X is used as a prothrombin activator.

53. The method as claimed in claim 51, wherein cattle prothrombin activators are used.

54. The method as claimed in claim 51, wherein the prothrombin activator is a non-human prothrombin activator.

55. The method as claimed in claim 54, wherein the snake venom is from *Notechis scutatus scutatus*.

56. The method as claimed in claim 51, wherein the prothrombin activator is snake venom.

57. The method as claimed in claim 56, wherein the snake venom is venom of *Notechis scutatus scutatus*.

58. The method as claimed in claim 57, wherein the snake venom is from *Vipera russellii*.

59. The method as claimed in claim 1, wherein one or more of reagents A, B and C are combined before being added to the sample.

60. The method as claimed in claim 59, wherein the sample is brought into contact with 2 reagents.

61. The method as claimed in claim 59, wherein the sample is brought into contact with 1 reagent.

62. The method as claimed in claim 1, wherein reagent A contains one or more of the following additives: protein S, factor X, prothrombin, or phospholipids.

* * * * *

UNITED STATES PATENT AND TRADEMARK OFFICE
CERTIFICATE OF CORRECTION

PATENT NO.   : 6,090,570
DATED        : July 18, 2000
INVENTOR(S)  : Kraus

It is certified that error appears in the above-identified patent and that said Letters Patent is hereby corrected as shown below:

Title page,
Item [57], in the ABSTRACT,
Line 1, "Method" should read -- The invention relates to a method --.

Column 16, claim 26,
Line 59, after "mixing with the", insert -- sample --.

Column 17, claim 34,
Line 15, "claim 19" should read -- claim 33 --.

Column 17, claim 38,
Line 24, "step C" should read -- step c --.

Column 18, claim 58,
Line 38, "claim 57" should read -- claim 56 --.

Signed and Sealed this

First Day of January, 2002

Attest:

JAMES E. ROGAN
Attesting Officer    Director of the United States Patent and Trademark Office